(12) United States Patent
Stefanski

(10) Patent No.: US 9,248,237 B2
(45) Date of Patent: Feb. 2, 2016

(54) INDICATION MECHANISM FOR AN AUTOMATIC APPLICATOR, PARTICULARLY FOR INSULIN

(71) Applicant: COPERNICUS Sp. z o.o., Szczecin (PL)

(72) Inventor: Adam Stefanski, Gniezno (PL)

(73) Assignee: Copernicus SP. ZO. O. (PL)

( * ) Notice: Subject to any disclaimer, the term of this patent is extended or adjusted under 35 U.S.C. 154(b) by 0 days.

(21) Appl. No.: 14/523,012

(22) Filed: Oct. 24, 2014

(65) Prior Publication Data

US 2015/0045737 A1 Feb. 12, 2015

Related U.S. Application Data

(63) Continuation of application No. 13/362,578, filed on Jan. 31, 2012, now Pat. No. 8,894,619, which is a continuation of application No. PCT/EP2010/054125, filed on Mar. 29, 2010.

(30) Foreign Application Priority Data

Jul. 31, 2009 (PL) .......................... 388694

(51) Int. Cl.
*A61M 5/00* (2006.01)
*A61M 5/31* (2006.01)
*A61M 5/20* (2006.01)
*A61M 5/315* (2006.01)

(52) U.S. Cl.
CPC ............... *A61M 5/3129* (2013.01); *A61M 5/20* (2013.01); *A61M 5/3155* (2013.01); *A61M 5/31543* (2013.01); *A61M 5/31553* (2013.01); *A61M 5/31556* (2013.01); *A61M 5/31583* (2013.01); *A61M 2005/2026* (2013.01); *A61M 2005/3126* (2013.01); *Y10T 29/49* (2015.01)

(58) Field of Classification Search
CPC .............. A61M 5/00; A61M 5/31515; A61M 5/31511; A61M 5/3129; A61M 5/16881; A61M 2005/3289; A61M 25/104; A61M 25/10; A61M 2025/1052; A61M 39/045; A61M 39/26
USPC ............................... 604/228, 189, 95.04, 246
See application file for complete search history.

(56) References Cited

U.S. PATENT DOCUMENTS

2005/0137571 A1 6/2005 Hommann

FOREIGN PATENT DOCUMENTS

| EP | 0338806 | 10/1989 |
|---|---|---|
| EP | 1351732 | 1/2004 |
| EP | 1645301 | 4/2006 |
| EP | 1819382 | 8/2007 |
| PL | 341395 | 4/2001 |
| PL | 375372 | 11/2006 |
| WO | 0062847 | 10/2000 |
| WO | 2006037434 | 4/2006 |
| WO | 2006084876 | 8/2006 |

*Primary Examiner* — Scott Medway
(74) *Attorney, Agent, or Firm* — Brinks Gilson & Lione

(57) ABSTRACT

The present disclosure concerns an indication mechanism for an automatic applicator, particularly for insulin or other liquid preparations, particularly for multiple injection administration of set doses of a medicine from an exchangeable container, for example for the self-application of insulin by diabetes patients. An indication mechanism for an automatic applicator, having an assembly of at least two barrels movably coupled to each other has an indication barrel mounted on the driving barrel contains only marking on its external surface and is co-axially connected to the pull-push control nut.

15 Claims, 7 Drawing Sheets

A-A

B-B

INDICATION MECHANISM FOR AN AUTOMATIC APPLICATOR, PARTICULARLY FOR INSULIN

CROSS-REFERENCE TO RELATED APPLICATIONS

Figure 1:
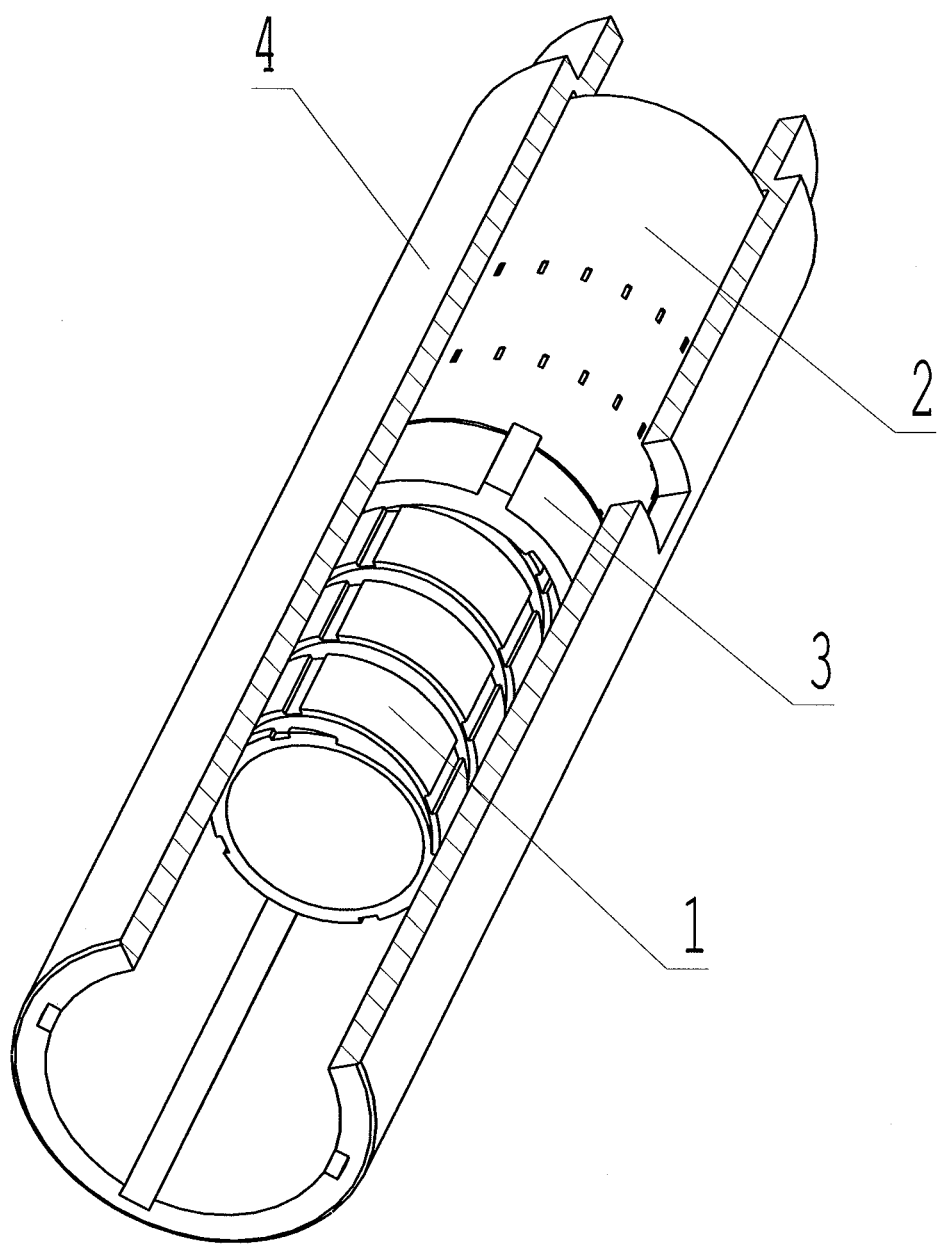

This application is a continuation of U.S. patent application Ser. No. 13/362,578 filed on Jan. 31, 2012, which is a continuation of International Application No. PCT/EP2010/054125 filed on Mar. 29, 2010, which claims the benefit of P 388694, filed Jul. 31, 2009. The disclosures of the above applications are incorporated herein in their entirety by reference.

FIELD

The present disclosure concerns an indication mechanism for an automatic applicator, particularly for insulin or other liquid preparations.

BACKGROUND

The statements in this section merely provide background information related to the present disclosure and may not constitute prior art.

The European patent EP 0338 806 A1 (Holman and Marchall) teaches a syringe comprising a body, a dose-setting device in the form of a rotary cap or ring mounted on the body and capable of being moved to a selected set position where a latch is arranged to retain the setting device in that set position, the movement of the setting device being accompanied by straining of a spring, which, when the latch is released, provides the force for expelling the set dose, characterised by means arranged to release the latch, which causes the return of the setting device to an original position to drive a plunger through a one-way clutch to expel the set dose; and by a quick pitch screw thread arrangement capable of transforming rotation of the setting device into linear movement of the plunger.

The indication mechanism in this syringe is designed in such way, that the displacement of the plunger is obtained by using the energy gathered in a helical spring, which is twisted, during the preliminary setting of the dose to be injected, by means of the rotation of a rotary cap or ring, which is rotateably mounted on sleeve having a degree scale at the right end of the syringe "pen" body. The rotary cap or ring has an inspection window showing an angle of the rotation of the said rotary cap or ring to be read from the scale.

The main disadvantage of the mechanism consists in that the scale comprises at the most only one complete rotation, which does not ensure its adequate precision.

Also Polish patent application P 341 395 teaches a syringe for distribution of set doses of a medicine from a cartridge containing the amount of the medicine sufficient to prepare several treatment doses, comprising a housing, a piston rod having noncircular cross-section and an external screw thread, a piston rod drive arrangement comprising two elements, i.e. piston rod leaders and a nut with an internal screw thread corresponding to the piston rod external screw thread, as well as a dose-setting mechanism comprising non-self-blocking screw thread connection, along which an injection push-button is unscrewed from the nearer housing end, causing rotation of the dose-setting element. This syringe is characterized in that between the nut and the piston rod leaders there is unidirectional coupling enabling the rotation of both these parts in one direction but not in the opposite direction, wherein the allowed rotation is the only one, by means of which the piston rod is moved in the circumferential direction in the syringe. The coupling is designed in such way that the initial resistance, sufficient to resist the torque exerted on the coupling by setting a dose, has to be overcome to allow rotation.

The indication mechanism in this syringe is designed in such way, that a convex spiral rib, constituting a quick thread, is formed on the internal wall of the second part of the housing. On the external wall of the dosing barrel having a scale there are spiral grooves defining external thread matching the internal thread of the housing. The pitch of the threads exceeds the friction angle form the materials of the threaded parts, therefore the coupling is not self-blocking and causes one part of the coupling to rotate, when another part is displaced linearly. Numbers indicating the set doses are printed on the external wall of the dosing barrel, and indicated in a window situated in a side wall of the housing.

The European patent EP 1 351 732 A1 (ENGGAARD CHRISTIAN) teaches a dose setting device for use in combination with a fluid-filled reservoir, the dose setting device being adapted for repetitive injection of individually set doses of fluid from the reservoir, the dose setting device comprising: a housing, a drive member adapted to expel a dose of medicine from the reservoir, a spring means, a dose setting assembly mounted in the housing and connected to the spring means, the dose setting assembly comprising a dose setting member being moveable in a first direction to a selected set position against the bias of the spring means, wherein movement of the dose setting member is accompanied by straining of the spring, and wherein the dose setting member is moveable in a second direction to selectively adjust the set dose, a latch means associated with the housing to retain the apparatus in the set position against the bias of the spring means, and the latch means being releasable to cause the drive member to expel the set dose from the syringe, the force for expelling the set dose being provided by the spring means.

The dose setting member comprises a foremost end wall and a rearwardly arranged skirt portion. The end wall has an opening with an internal thread, the end wall thereby serving as a second nut member through which the plunger is arranged. The thread corresponds to the internal thread thus allowing non-locking rotation of the plunger. The end wall further comprises a rearwardly facing coupling surface to be described below. The skirt portion of the dose setting member comprises longitudinal grooves on its inner surface engaging corresponding longitudinal tongue members on the outer surface of the skirt portion of the knob, whereby the two skirt members are allowed to slide axially but not to rotate relative to each other. Indeed, any suitable configuration could be used to provide this functional relation between the two skirt members. Numbers (not shown) are printed along a helical line on the external surface of the skirt which can be inspected through a window in the housing of the device, the window allowing only a portion, preferably only one, of the numbers on the sleeve to be inspected.

The Polish patent application P 375 372 discloses an automatic applicator particularly for insulin, more particularly for multiple injection application of set doses of a medicine from an exchangeable container, comprising a body housing connected to a housing of an exchangeable container with a medicine, particularly insulin, expelled by a piston connected to a plunger and displaced linearly by means of a leading and blocking driving unit driven via a double clutch unit by a tensioning spring situated in the body housing, tensioned by a rotary hand-dose-setting ring also via a double clutch unit, wherein a leading and blocking driving unit is activated by a trigger unit and a displaceable indicating cylinder is situated on the tensioning spring holder. According to the invention the said automatic applicator is characterized in that the double clutch unit comprises a clutch plate coupled co-axially with a body of the ratchet plate and coupled with pawls having catches meshed disengagingly with a gear ring of a driving nut.

The dose setting mechanism comprises the displaceable indicating cylinder, situated on the tensioning spring holder, is mounted slidingly, coaxially, in the tensioning spring holder groove and has a helical groove on its external surface mated with the internal screw thread of the body housing. Such construction provides for the dosage scale, displaced suitably at the dose-setting, to be well visible through a dose-setting inspection window. Besides, the displaceable indicating cylinder comprises the dose-setting end indicator in the form of a red dot, collaborating with the dose-setting end indicator window opening, provided with the dose-setting end indicator window. The currently set dose can be seen on the displaceable indicating cylinder with the scale through the dose-setting inspection window opening. The cylinder is scaled by every unit and the turning of the rotary hand-dose-setting ring is accompanied by a characteristic clicking at every unit, corresponding to 0.01 ml of insulin. The dose-setting can be realized up to a single unit, wherein the scale visible through the dose-setting inspection window, stops at any value or between the given dose values, as indicated by the arrow of the dose indicator on the housing.

The European patent application EP 1 819 382 A1 (MOLLER CLAUS SCHMIDT and MARKUSSEN TOM HEDE) teaches an injection device a housing with an inner surface provided with threads, a dose setting member adapted to set a dose to be ejected from the injection device, a torsion spring operatively connected to the dose setting member, such that energy is accumulated in the torsion spring upon rotation of the dose setting member, having a rotatably mounted display member threadedly engaged with the threads of the housing and operatively connected with the dose setting member and adapted to display the dose to be ejected from the injection device in accordance with a setting of the dose setting member, the rotateably mounted display member being rotatable over an angle corresponding to at least one revolution of the display member.

The dose setting mechanism of this device comprises the inner surface of housing of the injection device provided with threads. These threads are adapted to engage and co-operate with outer threads of a dose indicator barrel. The dose indicator barrel engages with sliding track of the dose setting member in such a way that the dose indicator barrel is able to slide in said sliding track in an axial direction of the injection device. When the dose setting member is rotated in order to set a dose, the dose indicator barrel rotates with the dose setting member causing the dose indicator barrel to be axially displaced relative to the housing. A window is provided in the housing of the injection device. Through this window, the user of the injection device may view the actual dose setting level from numerals (not shown) provided on an exterior surface of the dose indicator barrel. The numerals are arranged along a helical path.

The main disadvantage of the known devices is lack of the provision of application of the precisely controlled and set dose of a medicine. Earlier designs (e.g. acc. To EP 0 338 806) comprise a scale situated only on one circumference and allow only the placement of the small size prints of indication numerals. Also later, above discussed, designs having a spiral scale on the indication barrel do not fulfill their tasks adequately. Due to the large friction during the displacement along the thread of the housing wall, the precision setting of a dose is difficult. Also, due to the thread crisscrossing the external wall of the indication barrel, the placement on it of the adequately big size prints of indication numerals is not possible.

SUMMARY

In relation to the predicted applications of the present disclosure, particularly in the case of self-administration of insulin by diabetic users, diabetes causes significant sight disability. In such context the presence of a thread on the scale constitutes a drawback that matters, which leads to difficulty in reading the size of a dose. Lenses and magnifying glasses used in inspection windows deform the read numerals and do not present the satisfying solution of this problem.

Further, the thread which occupies the surface area destined for the scale reduces the number of numerals, which can be placed there. The extension of the scale to compensate for the loss of the surface area due to the thread, leads to overextension of the whole application device making it unhandy or even unsuitable for its use. A scale should obviously be legible but compact.

The existence of threads constitutes a technological obstacle because of the necessity to place the prints of numerals only between the threads, i.e. along a helical line. It makes difficult to situate important for the users marks, e.g. the mark indicating the end of insulin administration, in the most advantageous position on the scale.

The present disclosure concerns an indication mechanism for an automatic applicator, particularly for insulin or other liquid preparations, particularly for multiple injection administration of set doses of a medicine from an exchangeable container, is to ensure a capability for the precisely controlled setting and indication of a set dose of a medicine, preserving an automatic administration of the medicine without stress and without medicine losses, as reflux formed while dose setting, particularly by reducing the internal friction forces in the mechanism.

The present disclosure also ensures a capability to deposit adequately large prints on the scale, in any numbers and with any configuration of signs and indication numerals by the removal from the indication barrel surface any elements restricting its area.

The present disclosure further provides an indication mechanism suitable for an applicator with the possible number of the doses to be set greater than in the known devices of such kind.

An indication mechanism for an automatic applicator, particularly for insulin or other liquid preparations, particularly for multiple injection administration of set doses of a medicine from an exchangeable container, comprising an assembly of at least two barrels movably coupled to each other according to the present disclosure is characterized in that the indication barrel mounted on the driving barrel contains only marking on its external surface and is co-axially connected to the pull-push control nut.

Advantageously, the indication barrel is mounted slidingly, co-axially and lengthwise on the driving barrel by means of a key coupling, advantageously a splined coupling comprising the grooves and the keys, more advantageously splined coupling comprising bayonet keys.

Advantageously, the indication barrel is mounted slidingly between its two end positions defining the working range of the indication barrel. Further, advantageously, the driving barrel is mounted rotateably.

Advantageously, the pull-push control nut is mounted rotateably on the driving barrel by means of a thread coupling, advantageously having non selflocking thread.

Advantageously, the pull-push control nut is mounted slidingly, co-axially and lengthwise in the applicator housing by means of a key coupling, advantageously a splined coupling.

Advantageously, the indication barrel is mounted lengthwise to the pullpush control nut by means of a catch unit, advantageously a circumferential catch unit comprising the indication barrel catch and the control nut catch.

Advantageously, the indication barrel is mounted on the driving barrel with its external surface situated at the defined distance from the internal surface of the applicator housing.

Advantageously, the indication marking on the external surface of the indication barrel is in the form of indication numerals deposited spirally.

Advantageously, the driving barrel is connected to a driving element in the form of resilient means, advantageously in the form of the helical spring.

Advantageously, the driving barrel is connected to a mechanism for medicine dose setting.

DRAWINGS

Figure 2:
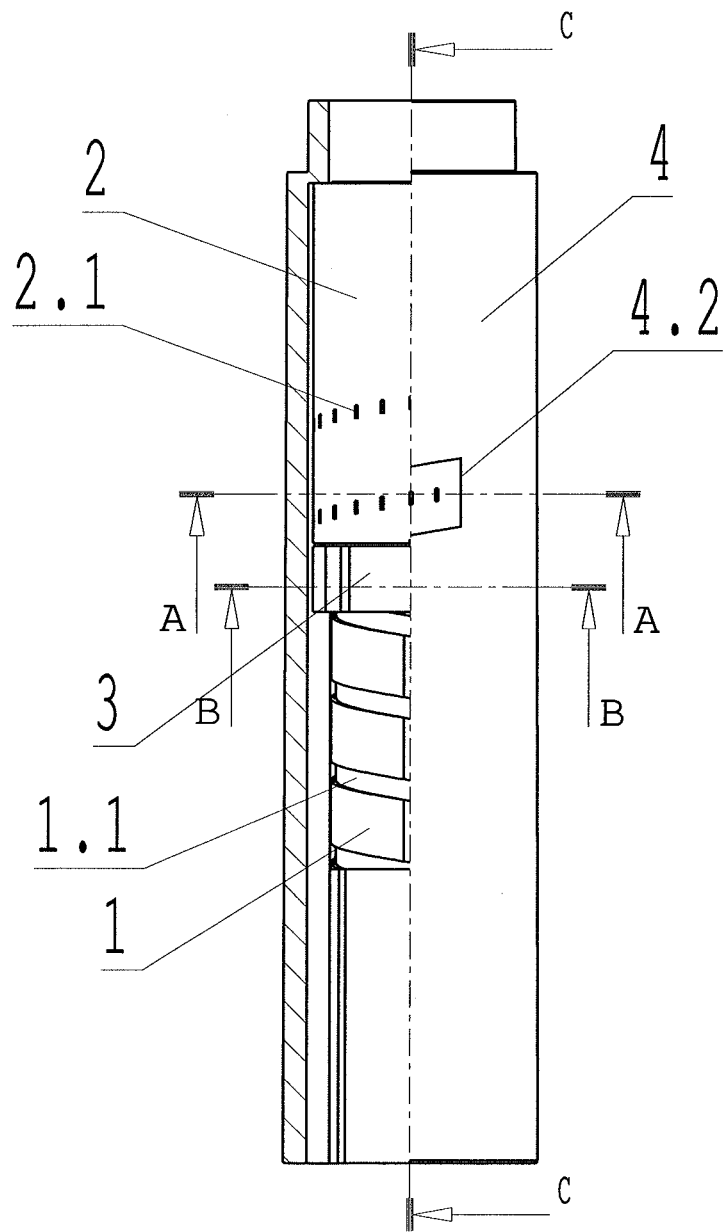
Figure 2A:
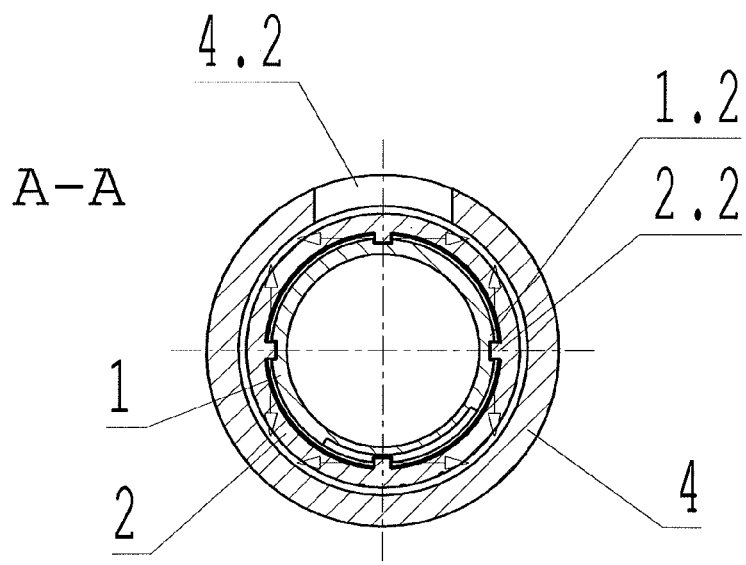
Figure 2B:
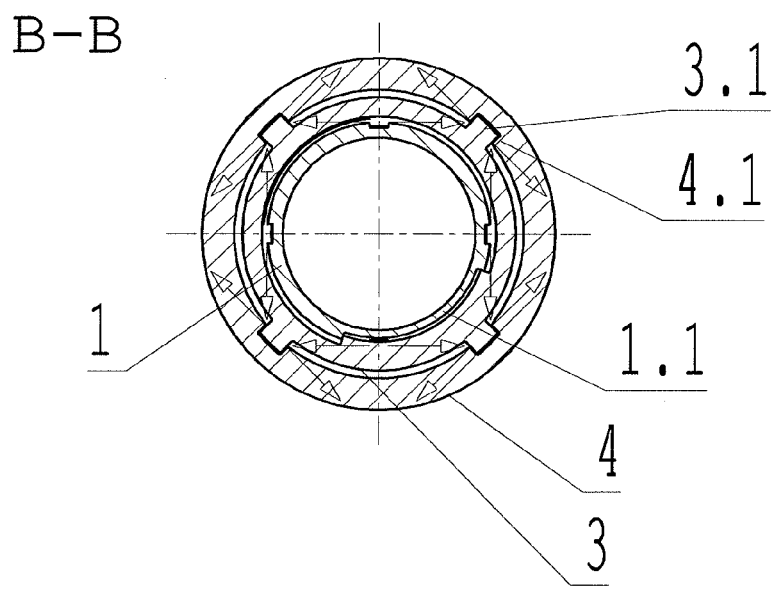
Figure 2C:
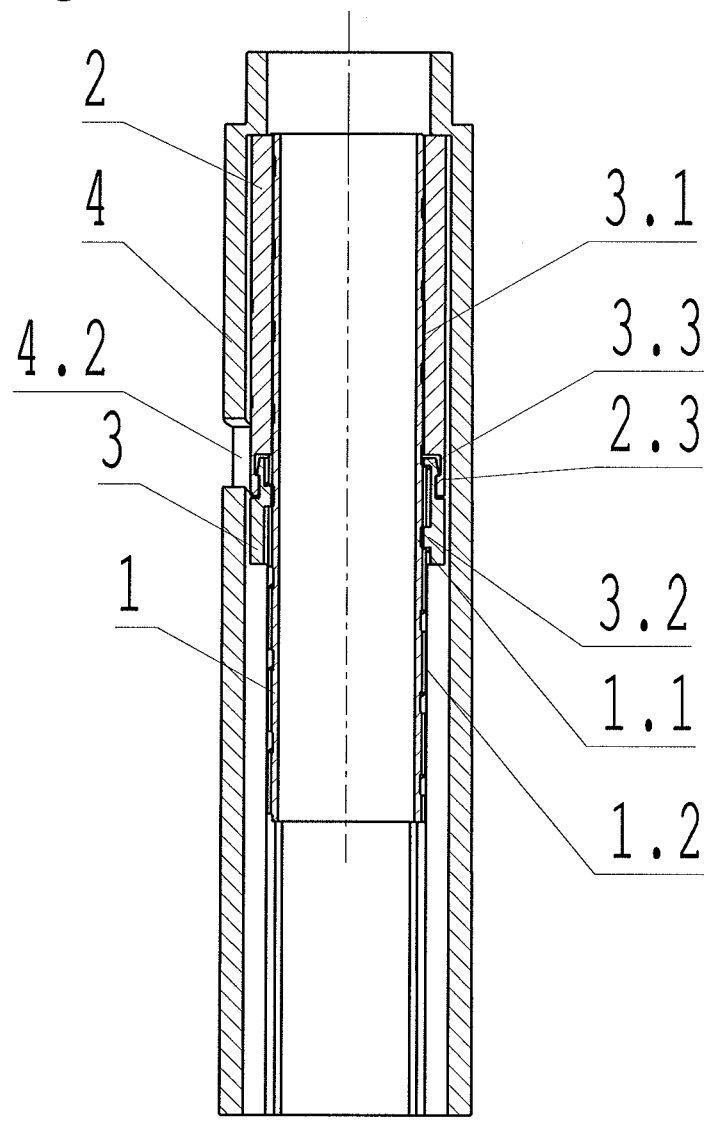
Figure 3:
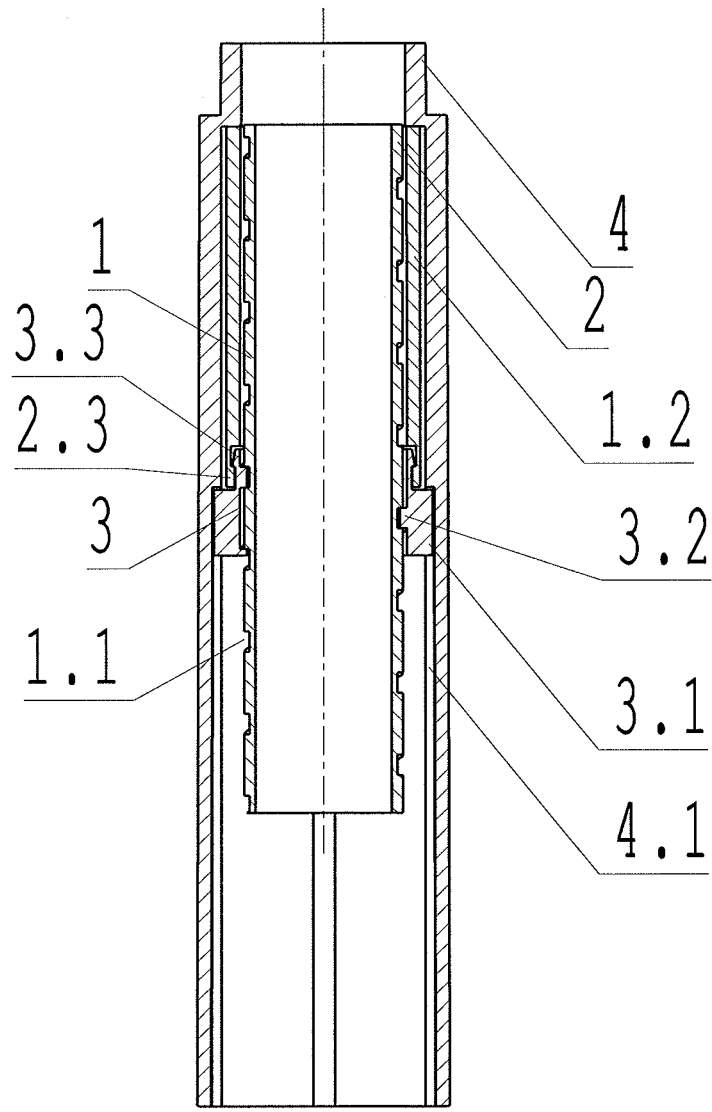
Figure 4:
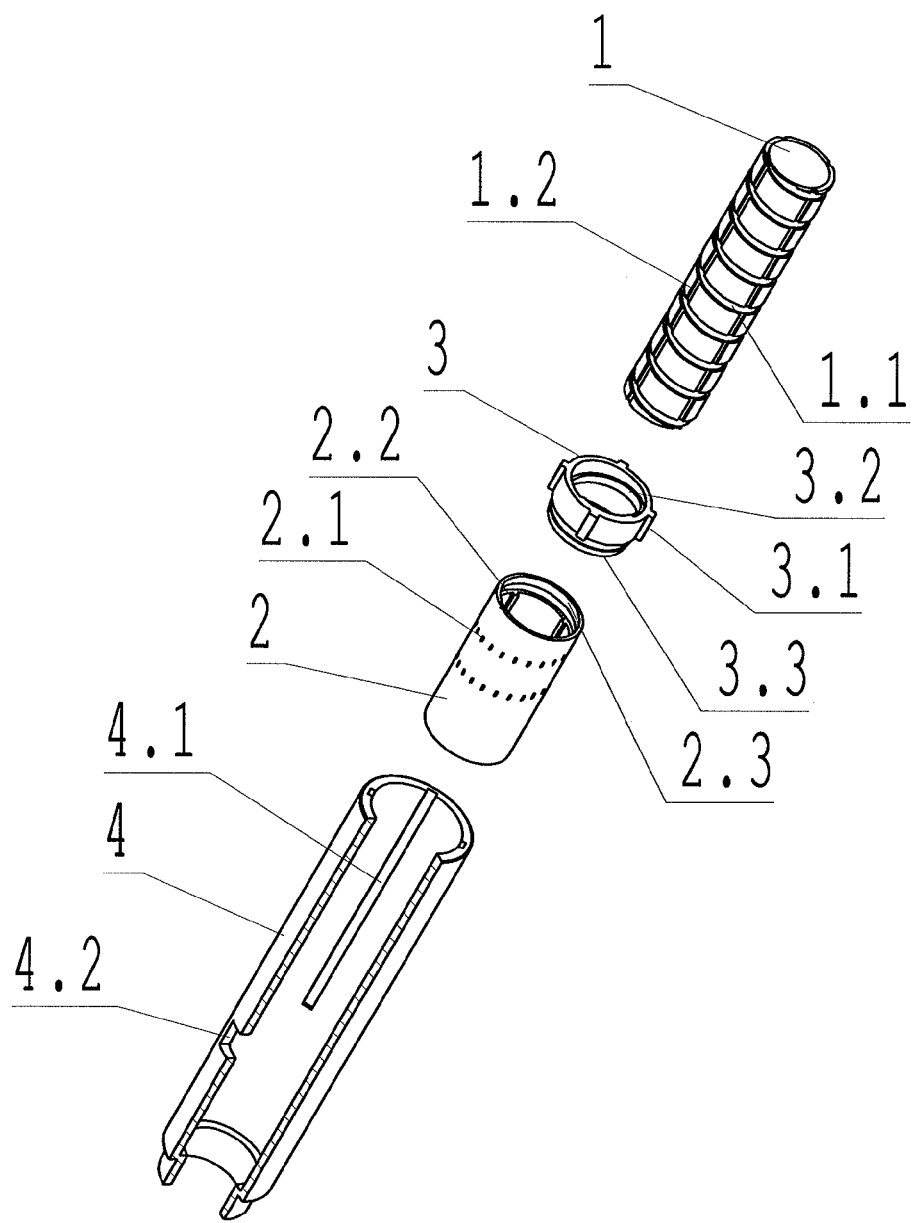
Figure 5:
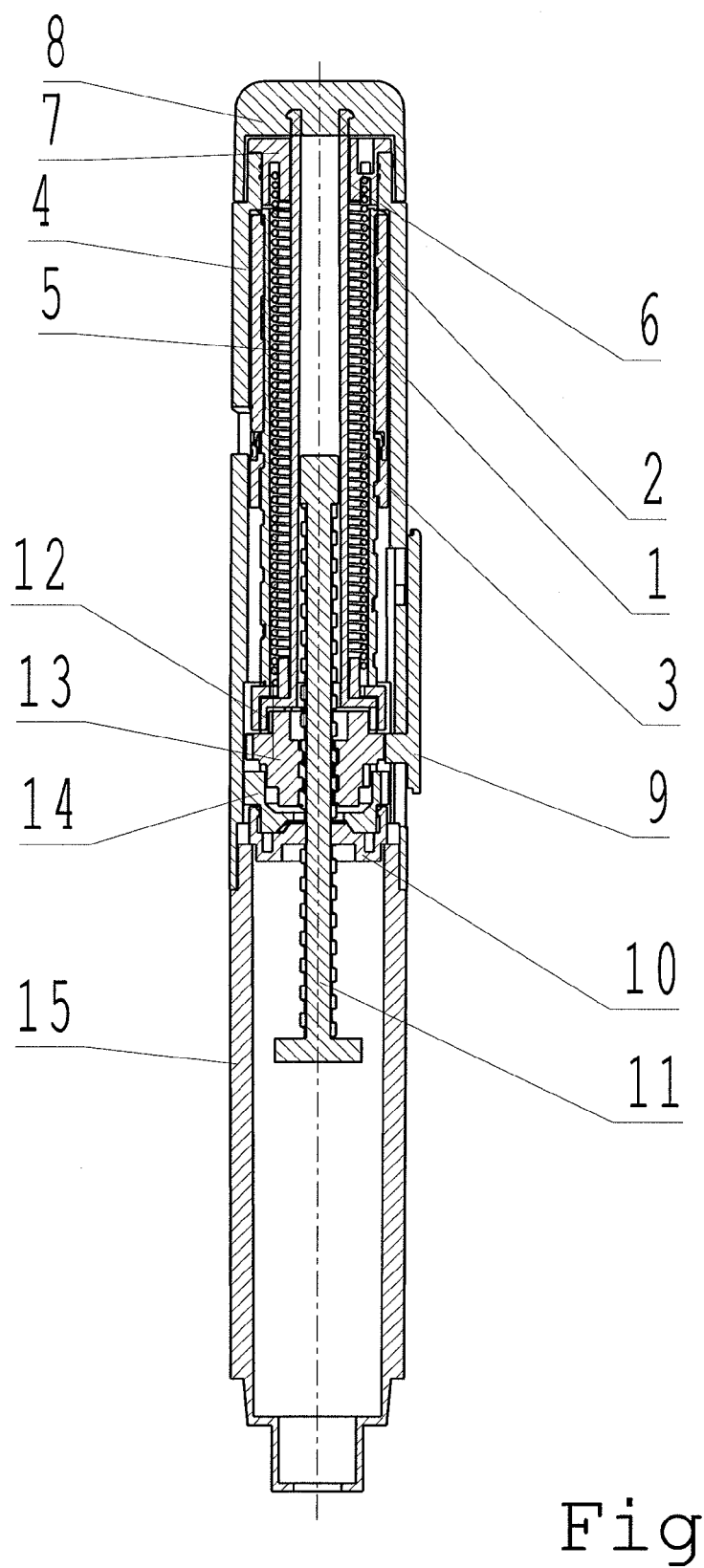

In order that the disclosure may be well understood, there will now be described various forms thereof, given by way of example, reference being made to the accompanying drawings, in which:

FIG. 1 presents the front axonometric view of the assembled indication mechanism for an automatic applicator, with parts of the housings removed;

FIG. 2 presents the longitudinal half-section of the indication mechanism;

FIG. 2A presents the cross-section A-A of the indication mechanism for an automatic applicator;

FIG. 2B presents the cross-section B-B of the indication mechanism for an automatic applicator;

FIG. 2C presents the longitudinal section C-C of the indication mechanism for an automatic applicator;

FIG. 3 presents the cross-section 0-0 of the indication mechanism for an automatic applicator, displaced by the angle of 45 deg. from the position shown in the longitudinal section C-C;

FIG. 4 presents the side axonometric exploded view of the indication mechanism for an automatic applicator, with parts of the housings removed; and FIG. 5 presents the automatic applicator with the indication mechanism according to the present disclosure.

DETAILED DESCRIPTION

The following description is merely exemplary in nature and is not intended to limit the present disclosure, application, or uses.

As shown in the FIG. 1 the indication mechanism for an automatic applicator for liquid pharmaceutical preparations, particularly for insulin, more particularly for multiple injection administration of set doses of a medicine from an exchangeable container, comprises an assembly of at least two barrels movably coupled to each other, wherein the indication barrel 2 mounted on the driving barrel 1 contains only marking 2.1 (FIG. 2) on its external surface and is co-axially connected to the pull-push control nut 3. The whole mechanism is placed in the housing 4. As presented in the FIG. 1, FIG. 2, FIG. 2A, FIG. 2B, FIG. 2C, FIG. 3 and FigA, the indication barrel 2 is mounted slidingly, co-axially and lengthwise on the driving barrel 1 by means of a splined coupling here comprising the grooves 1.2 of the driving barrel 1 and the keys 2.2 of the indication barrel 2, wherein the keys 2.2 are bayonet keys.

The indication barrel 2 is mounted slidingly between its two end positions defining the working range of the indication barrel 2. The driving barrel 1 is mounted rotateably. The pull-push control nut 3 is mounted rotateably on the driving barrel 1 by means of a thread coupling here comprising the thread groove 1.1 of the driving barrel 1 and the internal thread rib 3.2 of the control nut 3, advantageously having non selflocking thread. The pull-push control nut 3 is mounted slidingly, co-axially and lengthwise in the applicator housing 4 by means of a splined coupling, advantageously the splined coupling comprising the grooves 4.1 of the housing 4 and the keys 3.1 of the control nut 3.

The indication barrel 2 is mounted lengthwise to the pull-push control nut 3 by means of a catch unit, advantageously a circumferential catch unit comprising the indication barrel catch 2.3 of the indication barrel 2 and the control nut catch 3.3 of the control nut 3. The indication barrel 2 is mounted on the driving barrel 1 with its external surface situated at the defined distance from the internal surface of the applicator housing 4, wherein the housing 4 comprises the inspection window 4.2. The indication marking 2.1 on the external surface of the indication barrel 2 is here in the form of indication numerals deposited spirally. The driving barrel 1 is connected to a driving element in the form of resilient means, here in the form of the helical spring 5 (FIG. 5).

As shown in the FIG. 5, the driving barrel 1 is connected to a mechanism for medicine dose setting in the form of the assembly comprising the turning knob 8, the clutch 6, the resilient element, here the helical spring 5, the spring element block 7, the plunger 11, the ratchet mechanism 12, the nut 13, the plunger blocking sleeve 14, the plunger block 10, the trigger 9 and the container housing 15.

The indication mechanism for an automatic applicator for liquid pharmaceutical preparations, particularly for insulin, more particularly for multiple injection application of set doses of a medicine from an exchangeable container, operates as follows.

When a dose is to be set, the driving barrel 1 is turned clockwise, looking in the direction of the needle, (increase setting) or anti-clockwise (correction setting), wherein the control nut 3 is displaced along the driving barrel 1 by means of the thread coupling comprising the internal thread rib 3.2 of the control nut 3 moving in the thread groove 1.1 cut in the external wall of the cylindrical driving barrel 1. The pull-push control nut 3 is secured against rotation by means of the keys 3.1, which are displaced co-axially in the corresponding grooves 4.1 made in the internal cylindrical wall of the housing 4. Such connection enables preserving increased clearance between the external cylinder of the control nut 3 and the internal cylindrical wall of the housing 4, which contributes to the elimination of friction between these two cylindrical parts, which is much smaller owing to the co-axial sliding movement of the keys 3.1 in grooves 4.1, keeping the indication mechanism in the central point of rotation by means of the forces indicated by arrows in FIG. 2B.

The control nut 3 while moving along the housing 4 pulls behind it (during the increase setting) or pushes in the opposite direction (during the correction setting) the indication barrel 2 by means of the control nut catch 3.3 of the control nut 3 connected for rotation to the corresponding indication barrel catch 2.3 of the indication barrel 2. The indication barrel 2 performs resultant motion, as it is pulled or pushed by the control nut 3 in the co-axial direction and simultaneously rotates together with the driving barrel 1 as it is coupled to it by means of its keys 2.2 and the grooves 1.2 on the external wall of the cylindrical driving barrel 1. Such connection enables preserving increased clearance between the external cylinder of the driving barrel 1 and the internal cylindrical wall of the indication barrel 2, which contributes to the elimination of friction between these two cylindrical parts, which is much smaller owing to the co-axial sliding movement of the keys 2.2 in grooves 1.2, keeping the indication mechanism in the central point of rotation by means of the forces indicated by arrows in FIG. 2A and FIG. 2B. The resultant motion of the indication barrel 2 is a spiral movement against the inspection window 4.2 in the housing 4, which allows any number of complete rotations of the indication barrel 2 against the housing 4 within the range of the displacement of the indication barrel 2 against the driving barrel 1.

It is to be stressed that the direction of rotation can be changed so, that increase setting is obtained by turning the driving barrel 1 in the anti-clockwise direction. In such configuration the decrease setting can be obtained by turning the driving barrel 1 in the clockwise direction.

The construction of the present indication mechanism for an automatic applicator is based on the principle of collaboration cylinders joined by the splined couplings in such way, that there is no friction between the cylindrical surfaces of the elements. Owing to this, the forces from other, driving and/or resilient elements can be smaller, which lead to more uniform operation of an applicator during the processes of dose setting and dose administration. Ideal axial alignment of collaborating elements, ensured by means of splined couplings, positively affects the precision of medicine administration, which eliminates formation of reflux while dose setting, decreasing the actually administrated dose, and allowing the administrated dose to be exactly as set.

Another aspect of the present disclosure is the triple coupling of the indication elements of an automatic applicator, i.e. mutual cooperation of the indication barrel 2 with the driving barrel 2 and the control nut 3, in the way allowing for the precise and controlled decreasing of the incorrectly set dose, preserving an automatic administration of the medicine without any stress, ensuring long term usage of the automatic applicator, particularly for insulin, more particularly for multiple injection administration of set doses of a medicine from an exchangeable container.

What is claimed is:

1. An automatic applicator for liquid pharmaceutical preparations, the applicator comprising:
    an applicator housing; and
    an indication barrel;
    wherein the indication barrel contains a dose scale on an external surface, in the form of spirally disposed indication numerals, to indicate the set dose at an inspection window fixed in the applicator housing;
    wherein the indication barrel is mounted slidingly, co-axially and lengthwise directly on an external surface of the driving barrel in the applicator housing between two end positions defining a working range of the indication barrel, by a splined coupling comprising a plurality of keys located on the internal surface of the indication barrel and extending more than half of the length of the indication barrel, the longitudinal axis of the keys being arranged parallel to a longitudinal axis of the driving barrel;
    wherein the driving barrel is mounted rotatably within the applicator housing and is connected to a driving element in the form of a helical spring and to a mechanism for medicine dose setting that comprises a trigger used in conjunction with the helical spring.

2. The applicator according to claim 1, wherein the keys in the splined coupling are bayonet keys.

3. The applicator according to claim 1, wherein the indication barrel is mounted on the driving barrel with its external surface situated at a predefined distance, greater than zero, from the internal surface of the applicator housing.

4. The Applicator according to claim 1, wherein the driving barrel and the indication barrel are joined by the splined coupling such that there is no friction between the surfaces of the driving and indication barrels.

5. The Applicator according to claim 1, wherein the motion of the indication barrel is a spiral movement against the inspection window in the applicator housing; wherein such movement allows any number of complete rotations of the indication barrel against the applicator housing within the range of the displacement of the indication barrel against the driving barrel.

6. A method for indicating a set dose when using an automatic applicator for insulin liquid pharmaceutical preparations, the method comprising:
    rotating and displacing an indication barrel;
    wherein the indication barrel contains a dose scale on an external surface, in the form of spirally disposed indication numerals,
    wherein the indication barrel is being rotated and displaced to indicate the set dose with respect to an inspection window fixed in the applicator housing;
    wherein the indication barrel is mounted slidingly, co-axially and lengthwise directly on an external surface of the driving barrel in the applicator housing between two end positions defining a working range of the indication barrel by a splined coupling such that there is clearance between the external wall of the driving barrel and the internal wall of the indication barrel;
    wherein the indication barrel can be rotated and displaced within the working range over a plurality of rotations with respect to the applicator housing;
    wherein the working range of the indication barrel is within the housing;
    wherein the splined coupling comprises a plurality of keys located on the internal surface of the indication barrel and extending more than half of the length of the indication barrel, the longitudinal axis of the keys being arranged parallel to a longitudinal axis of the driving barrel;
    wherein the driving barrel is mounted rotatably within the applicator housing and is connected to a driving element in the form of a helical spring and to a mechanism for medicine dose setting that comprises a trigger used in conjunction with the helical spring;
    wherein the mechanism for medicine dose setting comprises a turning knob, said turning knob is turn-able and substantially axially immovable.

7. The method according to claim 6, wherein the keys in the splined coupling are bayonet keys.

8. The method according to claim 6, wherein the indication barrel is mounted on the driving barrel with its external surface situated at a predefined distance, greater than zero, from the internal surface of the applicator housing.

9. The method according to claim 6, wherein the driving barrel and the indication barrel are joined by the splined coupling such that there is no friction between the surfaces of these driving and indication barrels.

10. The method according to claim 6, wherein the motion of the indication barrel is a spiral movement against the inspection window in the applicator housing; wherein such movement allows any number of complete rotations of the indication barrel against the applicator housing within the range of the displacement of the indication barrel against the driving barrel.

11. An automatic applicator for liquid pharmaceutical preparations, the applicator comprising:
   an applicator housing; and
   an indication barrel;
   wherein the indication barrel contains a dose scale on an external surface, in the form of spirally disposed indication numerals, to indicate the set dose at an inspection window fixed in the applicator housing;
   wherein the indication barrel is mounted slidingly, co-axially and lengthwise directly on an external surface of the driving barrel in the applicator housing between two end positions defining a working range of the indication barrel by a splined coupling such that there is clearance between the external wall of the driving barrel and the internal wall of the indication barrel;
   wherein the working range of the indication barrel is within the applicator housing and comprises a plurality of rotations with respect to the applicator housing;
   wherein the splined coupling comprises a plurality of keys located on the internal surface of the indication barrel and extending more than half of the length of the indication barrel, the longitudinal axis of the keys being arranged parallel to a longitudinal axis of the driving barrel and disposed such that the indication barrel and the driving barrel are maintained in the central point of rotation and coaxially with the longitudinal axis of the housing;
   wherein the driving barrel is mounted rotatably within the applicator housing and is connected to a driving element in the form of a helical spring and to a mechanism for medicine dose setting that comprises a trigger used in conjunction with the helical spring.

12. The applicator according to claim 11, wherein the keys in the splined coupling are bayonet keys.

13. The applicator according to claim 11, wherein the indication barrel is mounted on the driving barrel with its external surface situated at a predefined distance, greater than zero, from the internal surface of the applicator housing.

14. The Applicator according to claim 11, wherein the driving barrel and the indication barrel are joined by the splined coupling such that there is no friction between the surfaces of the driving and indication barrels.

15. The Applicator according to claim 11, wherein the motion of the indication barrel is a spiral movement against the inspection window in the applicator housing; wherein such movement allows any number of complete rotations of the indication barrel against the applicator housing within the range of the displacement of the indication barrel against the driving barrel.

* * * * *